United States Patent [19]

Kong et al.

[11] Patent Number: 5,705,170
[45] Date of Patent: Jan. 6, 1998

[54] HERBAL CELLULITE TREATMENTS

[75] Inventors: William C. Kong, Whitestone, N.Y.; Raymond Yeung, Stamford, Conn.

[73] Assignee: Plantech International, Inc., College Point, N.Y.

[21] Appl. No.: 547,417

[22] Filed: Oct. 24, 1995

[51] Int. Cl.$^6$ .................................................. A61K 7/48
[52] U.S. Cl. ........................ 424/401; 414/195.1; 514/860
[58] Field of Search ............................ 424/401, 195.1; 514/860

[56] References Cited

U.S. PATENT DOCUMENTS 5,165,935  11/1992  Andre et al. ........................... 424/450
5,194,259   3/1993  Soudant et al. ....................... 424/401

OTHER PUBLICATIONS

Hortus Third, Liberty Hyde Bailey Hortorium, Macmiillan Publishing Co., Inc. (New York, NY, U.S.), 1976, pp. 1, 560, 702.

"Cellulite Treatments: Snake Oils or Skin Science" by Walter P. Smith, *Cosmetics & Toiletries* magazine, vol. 110 pp. 61 to 70 (Jul. 1995).

"Controlling the Appearance of Cellulite: AHAs and Cellulite Products" by Ronald M. DiSalvo, *C & T Ingredient Resource Series* pp. 21 to 27.

"Local Lipodystrophy and Districtual Microcirculation" by S.B. Curri et al., *Cosmetics and Toiletries*, vol. 109, pp. 51 to 53 (Sep. 1994).

*Primary Examiner*—Jyothsan Venkat
*Attorney, Agent, or Firm*—Handal & Morofsky

[57] ABSTRACT

The invention provides a herbal cellulite treatment employing, in preferred embodiments, topical treatments, both method and cosmetic composition, wherein a refined lipophilic extract, and preferably also a refined aqueous extract of a Malvaceae plant, preferably whole *Hibiscus Abelmoschus*, are applied to the skin overlying cellulite-afflicted tissues. The treatments are intended to last at least four, and preferably eight or more weeks. Clinical tests show suprisingly superior results to those obtainable with aminophylline compositions. Inventive treatments can reduce thigh diameters and fatty layer thickness, as well as skin condition. In vitro tests show remarkable lipolytic properties, apparently attributable to β-receptor stimulation, and valuable lipogenesis inhibition properties apparently attributable to $\alpha_2$-blocking. Preferred extracts show low toxicity.

13 Claims, 5 Drawing Sheets

HERBAL CELLULITE TREATMENTS

TECHNICAL FIELD

This invention relates to herbal cellulite treatments. Cellulite is a medical and cosmetic condition in which disorders of the skin and underlying tissues and vasculature lead to unsightly accumulations of adipose tissue. The treatments described herein employ non-toxic herbal extracts from a common plant source to obtain, valuable and in some cases surprising, reductions of the cellulite condition, especially as determined by measurements of tissue thickness. More particularly, the invention relates to herbal methods of treating cellulite are suitable for unsupervised consumer use, and to novel topically applied consumer use, cosmetic compositions for cellulite treatment, which compositions contain active herbal ingredients.

BACKGROUND

Cellulite afflictions are a stubborn problem causing emotional and psychological distress to many women. Cellulite primarily afflicts the thighs and buttocks but may also be present on the stomach and upper arms. Frequently, cellulite presents an unsightly, lumpy orange-peel appearance. Clinically, cellulite manifests a range of symptoms including thinning of the epidermis, reduction and breakdown of the microvasculature leading to subdermal accumulations of fluids, and subdermal agglomerations of fatty tissue.

Current scientific thinking postulates that fat particles stored within the cells in women's hips and thighs are more difficult to reduce because of an abundance of external cellular receptors whose activation inhibits lipolysis, the breaking down of fat.

Many treatments for cellulite have been devised and are directed at reducing the agglomerations of fatty tissue. While some treatments rely upon sweating to reduce fluid accumulations, and perhaps stimulate circulation, more effective treatments are more directly targeted to reducing the volume of the fatty deposits by, for example, massage with mechanical implements, or by application of topical treatments containing an active agent. Such topical treatments are usually accompanied by more or less massage. W. P. Smith in "Cellulite Treatments: Snake Oils or Skin Science" *Cosmetics & Toiletries* (trademark) magazine pages 61 to 70 (July 1995), "Smith C & T" herein, describes various stages of cellulite disorder in detail and reviews the efficacy of a number of cellulite treatments by reference to their ability to improve microcirculation, skin firmness and skin thickness, and to reduce thigh diameter.

Mechanism of action of anti-cellulite agents. Two receptors on the outer membranes surface of adipocytes (fatty cells) are believed to control the fat volume of the cell. These receptors are a $\beta$ receptor activation of which stimulates lipolysis and an $\alpha_2$ receptor, activation of which stimulates lipogenesis and inhibits lipolysis.

Lipolysis is a breaking-down of the fatty deposits and is therefore a very desirable mechanism to stimulate in any cellulite treatment while lipogenesis refers to a cell's ability to manufacture fatty materials. Clearly, lipogenesis is to be inhibited. Thus, according to these models, the $\beta$ receptor should be stimulated, $\beta$-adrenergic stimulation, and the $\alpha_2$ receptor should be inhibited, $\alpha_2$-adrenergic inhibition. These mechanisms are described in more detail in Di Salvo "Controlling the Appearance of Cellulite: AHAs and Cellulite Products" *C & T Ingredient Resource Series*, pages 21 to 27, and Curri "Local Lipodystrophy and Districtual Microcirculation" Cosmetics and Toiletries (trademark) magazine, volume 109, pages 51 to 53 (September 1994). Curri describes the symptomatic and anatomic pathology of cellulite in some detail, and urges that deterioration of the microvasculature leads to fatty accumulations, rather than vice versa. Di Salvo discloses methods and compositions for treating cellulite which are described more fully hereinbelow.

A further description of possible biochemical mechanisms relevant to cellulite therapy, which is based upon the disclosures of Di Salvo and Curri, also appears below and references FIG. 1 of the accompanying drawings.

Known anticellulite active agents. Adrenergic agents are substances that have an epinephrine- or norepinephrine-like adrenal stimulation function. The best known of these is caffeine which is one member of a class of substances known as xanthines. Caffeine and other xanthines, notably aminophylline and theophylline have been used in cellulite treatments with moderate efficacy.

These materials bind either directly or indirectly to the $\beta$-receptor, thereby stimulating it. The stimulated receptor triggers a complex series of events involving multiple enzyme systems which results in an accumulation of cyclic AMP within the cell and decreased ATP. These conditions activate lipases which break down triglyceride fats in the adipocytes into free fatty acids, which can be used by the cell for growth and metabolism, or may be discharged extracellularly.

The $\alpha_2$-receptor is regulated by other materials which usually do not themselves influence the $\beta$-receptor. The $\beta$-receptors exert a regulatory control over the $\beta$receptors so that stimulation of the $\beta$-receptors can only be partially effective, unless the $\alpha_2$-receptor is simultaneously inhibited.

Di Salvo reports, page 21, right-hand column, line 9 from the bottom, that topical application of a $\beta$-adrenergic stimulator and an $\alpha_2$-adrenergic inhibitor produces a blocking of lipolysis inhibition so that fatty acids are released more readily. Di Salvo points out that for this approach to be successful, the active agent or agents must be delivered (through the dermis) into the vicinity of the fatty deposits that are to be broken down.

Di Salvo discloses various adrenergic stimulators and adrenergic inhibitors. As listed by Di Salvo, the former are primarily the known $\beta$-receptor adrenergic stimulators listed above, namely pharmaceutical substances that include the hormone epinephrine, also known as adrenaline and analogs of epinephrine including xanthines, such as aminophylline, and caffeine. Although some compounds such as theophylline are derived from herbal sources such as cacao beans, kola nuts and tea leaves, they are all chemical isolates, or substances.

The $\alpha_2$-adrenergic inhibitors listed by Di Salvo are exotic plant alkaloids, also chemical isolates, fully identified as individual chemical substances, which have hypertensive or vasoconstrictive action. Exemplary compounds are yohimbine and dihydroergotamine. Unfortunately, these compounds are sourced from families of plant or fungal alkaloids which include some extremely poisonous members. They are rare and exotic, expensive and potentially dangerous. They are not suitable for unsupervised consumer use, nor are they suitable for formulating in topical cosmetic compositions. Di Salvo also reported greater thigh reductions in experimental treatments employing a silane, methylsilanetriol in conjunction with theophylline than was obtained with aminophylline alone. Although they may show some efficacy, with or without additional actives such as silanols, there are significant safety concerns regarding xanthines such as aminophylline and theophylline and it would be desirable to provide efficacious cellulite treatments that avoided the use of such questionable active ingredients.

Smith C & T, cited above, reports the results of comparative studies of a variety of cellulite treatments and finds that xanthines provide a modest perceivable and measurable improvement in cellulite over an eight-week test and that retinoids and AHA treatments improved skin attributes but provided only modest improvement in cellulite, whereas an unspecified herbal treatment and heat treatments produced no beneficial effects whatsoever. Accordingly, well-known, cosmetically compatible skin-improving ingredients such as AHAs and retinoids are not suitable alternatives to aminophylline or other xanthines. Nor, apparently, does stimulation of skin improvement necessarily correlate with anticellulite activity.

Known herbal anticellulite agents. Many people prefer to use herbal active ingredients rather than purified chemical substances or isolates, believing that the complexity of a biological material is more beneficial, or less likely to be harmful, or both. Di Salvo also discusses anticellulite properties of various herbal treatments in the context of their ability to reduce edema and provide tissue-decongestant and vasoactive activity, page 24, right-hand column. Such herbal treatments may improve local irrigation and removal of toxic wastes, leading to a reduction in edema and inflammation, if present. A list of 20 or 30 herbal extracts is presented and ivy, butcher's broom, seaweed and coconut extracts are cited in the text. However, there is no evidence in the Di Salvo article of herbal extracts having significant lipophilic activity of their own which might offer β-receptor stimulant efficacy comparable to, or better than, aminophylline and would lack the safety concerns associated with aminophylline. Nor does Di Salvo teach a satisfactory, herbal $\alpha_2$-blocker that can be used in topical consumer treatments, without safety concerns.

Various other plant-derived materials are known or have been suggested as having fat-reducing activity that would be useful in slimming treatments or cellulite treatments. For example, Andre et al in U.S. Pat. No. 5,165,935 report that kola seed extracts substantially free of methylxanthines have lipolytic activity, when determined in vitro, that is at least as active as kola extracts containing methyl xanthines, see for example column 2, lines 8–13. The activity of Andre's core extracts was determined, in vitro, on murine pre-adipocytes. Based on this data, Andre claim that a gel suspension of liposomes containing the subject kola extract, when applied daily to the waist, thighs and hips enables a substantial reduction of cellulitis in a period of one to three weeks, column 10 lines 5–41 but there is no data to support this claim.

Soudant et al disclose various plant-origin materials that have alphas-blocking activity and effectively divides them into two categories. A first category comprises yohimbine-type $alpha_2$-blockers which do not penetrate the skin well and may induce (undesirable) secondary effects, column 1, lines 44–55. A second category comprises plant-origin extracts such as ginkgo biloba, ivy and escine which show $alpha_2$-blocking activity, but must be used in high concentrations, column 1, lines 66–68. An ivy extract was tested, pursuant to the present invention, as a control, see Table 1 below, and found to have no significant lipolytic activity.

Thus the prior art known to applicant is devoid of a herbal treatment for cellulite which employs active herbal agents having lipolytic activity comparable with aminophylline.

There is accordingly a need for a herbal treatment for cellulite which is effective in reducing fatty deposits. Such a herbal treatment should do more than merely tone tissues and improve irrigation, and should desirably have significant lipolytic properties at least as good as aminophylline. This is not to suggest that aminophylline is a satisfactory active anticellulite ingredient, even aside from its non-herbal character and uncertain safety: superior performance providing a quicker reduction in cellulite would be highly desirable. Aminophylline is specifically addressed here because it is widely used in commercial anticellulite treatments and shows some efficacy.

A herbal cellulite treatment that employed safe, non-toxic herbal extracts (not poisonous plant or fungal alkaloids) and which provided better lipolytic activity than aminophylline would be especially desirable. Still more desirable would be a herbal treatment for cellulite that were capable of both stimulating lipolysis and inhibiting lipogenesis, for example by providing both β- receptor stimulation and $\alpha_2$-receptor inhibition.

SUMMARY OF THE INVENTION

The invention, as claimed, is intended to provide a remedy. It solves the problem of providing a non-toxic herbal cellulite treatment which can significantly reduce fatty deposits associated with cellulite.

Accordingly, the present invention provides a cellulite treatment composition comprising:

a) a cosmetic base;

b) from about 0.1 to about 10.0 percent by weight of the treatment composition of a refined aqueous extract of *Hibiscus Abelmoschus* rich in proteins; and c) from about 0.01 to about 10.0 percent by weight of the treatment composition of a refined lipophilic extract of *Hibiscus Abelmoschus* rich in sphingolipids the refined extracts being present in a relative proportion of from about 1 to about 7 parts of aqueous extract per part of lipophilic extract.

When properly constituted, having regard to the teaching herein, this composition is topically effective when applied to cellulite afflicted tissue to reduce fatty tissue deposits.

Stated differently, the invention provides a cellulite treatment composition comprising:

a) a cosmetic base;

b) a sufficient quantity of a refined aqueous extract of *Hibiscus Abelmoschus* to stimulate adipocyte lipolysis when the composition is applied topically to cellulite-afflicted tissue; and c) a sufficient quantity of a refined lipophilic extract of *Hibiscus Abelmoschus* to inhibit adipocyte lipogenesis when the composition is applied topically to cellulite-afflicted tissue.

*Hibiscus Abelmoschus*, common name "musk mallow" is a species of the mallow family, Latin name Malvaceae, in the order Malvales.

Compositions according to the invention can be formulated as a cosmetic composition intended for daily topical application and can provide a significant measurable improvement in cellulite after at least 8 weeks of daily topical application. Preferably, the composition comprises, in proportions by weight, from about 2 to about 5 percent of the refined aqueous *Hibiscus Abelmoschus* extract, from about 0.5 to about 3 percent of the lipophilic *Hibiscus Abelmoschus* extract, the composition being effective to stimulate adipocyte lipolysis and to inhibit adipocyte fat production. Experimental data described below show that compositions according to the invention are remarkably effective in reducing cellulite, as demonstrated by reductions in fatty deposits determined by comparative thigh diameter measurements. Other data show that the aqueous Malvaceae extract is an outstandingly effective β-stimulant promoting lipolysis, while the lipid Malvaceae extract is an excellent $\alpha_2$-blocker or inhibitor. This latter characteristic is especially valuable because the Malvaceae extracts, unlike other known plant-origin $\alpha_2$-blockers, have cosmetically acceptable toxicity characteristics and are readily absorbable through the skin for delivery where they are needed.

If desired, the composition can be supplemented with an effective quantity of an active agent or agents to improve microcirculation, improve skin condition or reduce fluid retention thereby providing a multi-functional cellulite treatment composition.

Such supplements are preferably selected from the group consisting of from about 0.1–20 percent by weight of the composition of an alpha hydroxy acid, the composition having a pH of from 3–6; a retinoid, in a proportion of from 0.1–3 percent, for example vitamin a palmitate; from about 0.1–5 percent by weight biopeptide; from about 1.0–20.0 percent by weight of a mechanical exfoliative; from about 1.0–5.0 percent by weight of a vasoactive ingredient; from about 1.0–5.0 of an antioxidant; and from about 2 to about 12 percent by weight of a moisturizer.

In another aspect, the invention provides a method of treating cellulite-afflicted tissue comprising the topical application of a cosmetic composition containing a sufficient quantity of a refined aqueous extract of *Hibiscus Abelmoschus* to stimulate adipocyte lipolysis.

Preferably, from about 0.1 to about 10.0 percent be weight of the aqueous extract of *Hibiscus Abelmoschus* is applied daily for at least four, or more preferably, to obtain more significant results, at least eight weeks.

The method preferably also comprises the topical application of a sufficient quantity of a refined lipophilic extract of *Hibiscus Abelmoschus* to inhibit adipocyte lipogenesis when the composition is applied topically to cellulite-afflicted tissue. Preferably, both the aqueous and lipophilic extracts of *Hibiscus Abelmoschus* are applied daily for at least eight weeks in a concentration of from about 0.1 to about 10.0 percent by weight of the applied composition.

In a further aspect, the invention provides a method of treating cellulite-afflicted tissue comprising the topical application of a cosmetic composition containing a sufficient quantity of a refined lipophilic extract of *Hibiscus Abelmoschus* to inhibit adipocyte lipogenesis when the composition is applied topically to cellulite-afflicted tissue. Preferably, the lipophilic extract of *Hibiscus Abelmoschus* is applied daily for at least eight weeks in a proportion of from about 0.1 to about 10.0 by weight of the applied composition.

The invention thus provides simple, easily applied and effective treatments for cellulite which derive their activity from herbal ingredients. The aqueous and lipophilic extracts of a suitable Malvaceae plant are not purified isolates but retain substantial biological complexity, as shown by analytical data such as thin-layer chromatograms. Preferred extracts have low toxicity, little color or odor, good stability and shelf life and are well suited for incorporation in cosmetics compositions that can be marketed to consumers for daily application at home, without professional supervision.

As reported hereinbelow, a tested aqueous extract of a Malvaceae plant showed good lipolytic activity, presumably via β-stimulation, and a lipophilic extract of the same plant showed good inhibition of lipogenesis, presumably via $alpha_2$-blocking or inhibition. The two extracts work well together and in clinical tests provide reductions in comparative thigh diameters and fatty layer thickness. Preferred extracts showed superior efficacy to tested known treatments including an aminophylline-based product and also including a crude Malvaceae extract. The latter was shown to lack the efficacy of the refined extracts.

The lipophilic extract is of particular value in cosmetics compositions and in cellulite or other treatments for inhibiting the production of triglycerides and the like in adipocytes, as being an active extracts having good efficacy and being "user-friendly", having the desirable cosmetic and other properties described above. Few such alpha-$_2$ blockers are known.

Extraction processes for producing preferred extracts from a suitable Malvaceae plant are described herein and an example of characteristic analytical data of a preferred embodiment is also provided. Suitable extracts are available from Plantech International Inc., Flushing, N.Y.

BRIEF DESCRIPTION OF THE DRAWINGS

Some illustrative embodiments of the invention, and the best mode contemplated of carrying out the invention, are described in detail below with reference to the accompanying drawings in which.

DETAILED DESCRIPTION OF THE PREFERRED EMBODIMENTS

Figure 1:
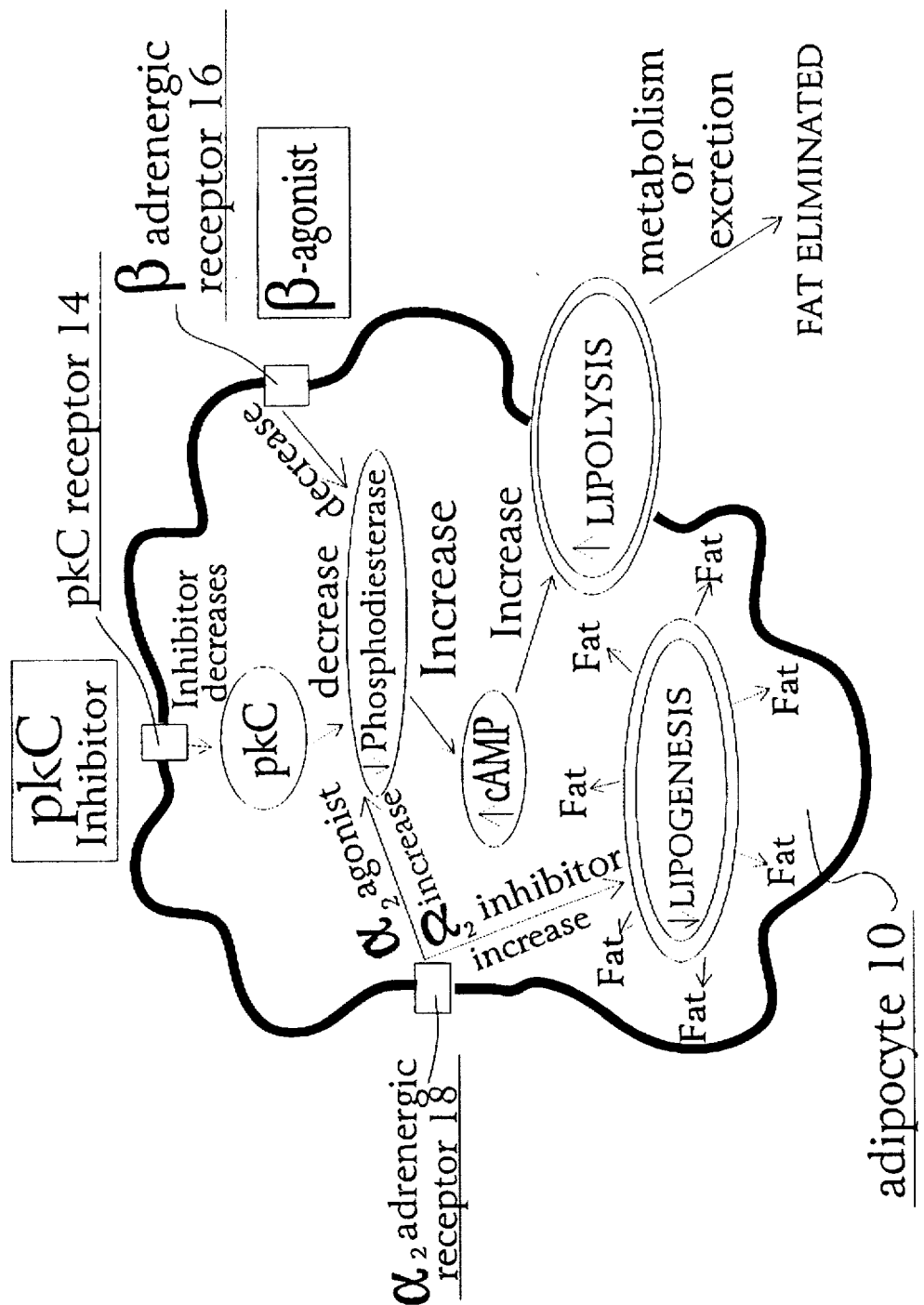
FIG. 1 is schematic diagram of an adipocyte, or fat cell, illustrating some possible biochemical reaction mechanisms leading to lipolysis, fat breakdown or lipogenesis, fat production.

Unless it is stated otherwise, or is apparent from the context that some other usage is intended, the terminological usage herein is intended to be consistent with that of the CTFA International Cosmetic Ingredient Dictionary (1991) published by the Cosmetic, Toiletries, and fragrance Association, Washington D.C. Also, unless otherwise indicated, proportions of ingredients are by weight and are based upon the total weight of the relevant composition.
Relevant Biochemical Mechanisms of Action FIG. 1 shows schematically some of the processes occurring in an adipocyte, or fat cell, in response to binding of various small molecules with receptors on the cell's membrane outer membrane surface. These processes may lead to the desirable process of lipolysis, or fat breakdown, or to the undesirable process of lipogenesis, or fat generation. FIG. 1 and the following description are intended to assist an understanding of possible mechanisms of action of the methods and compositions of the claimed invention, and more clearly to guide those skilled in the art as to what materials may be expected to be equivalents to the particular materials disclosed herein for use in practicing the invention, without limiting the invention, which is not dependent upon any particular theory as to the mode by which the desirable results, described herein, are obtained.

It will be understood that the processes of stimulation and inhibition of lipid generation and lipolysis are much more complex than shown in FIG. 1, and that the details of these processes are only poorly understood. Other mechanisms leading to lipolysis or lipogenesis also involve fundamental cellular mediators such as protein kinases and cyclic-AMP. Some of these processes are described in Di Salvo and Curri, cited above.

In FIG. 1 an adipocyte 10 is shown with three different types of receptors in its outer membrane 12, a pkC receptor 14, a β-adrenergic receptor 16 and an $\alpha_2$-adrenergic receptor 18. In FIG. 1, upwardly directed arrows indicate an increase in desired processes for the reduction of fat and cellulite, while downwardly directed arrows indicate an increase in undesired processes. Thus lipolysis is marked with an upward arrow and lipogenesis with a downward arrow. A β-agonist, or β-receptor activator or stimulator, is shown as binding with β-adrenergic receptor 16. This receptor binding blocks, or inhibits, phosphodiesterase production, leading to increased levels of cyclic-AMP which are known to trigger lipolysis. The outer membranes of adipocytes are liberally endowed with $\alpha_2$- and β-receptor cells as well as pkC receptors.

Lipolysis involves processes such as the breaking-down of triglycerides into small-molecule fatty adds which can be internally metabolized like the adipocyte, or excreted, resulting in elimination of the fat from the cell.

Unfortunately, this desirable process is subject to inhibition by agonists or stimulators binding with the $\alpha_2$-adrenergic receptor 18, which increase levels of phosphodiesterase, reducing cyclic-AMP availability and reducing lipolysis. The stubbornness of many cellulite afflictions may be explained by postulating that the action of β-agonists is subject to a companion $\alpha_2$-receptor stimulation which exerts a controlling influence over β-receptor mediated stimulation of lipolysis.

Thus, $\alpha_2$ inhibition is desirable. Inhibition or blocking of $\alpha_2$ receptors permits unhindered β-receptor mediated stimulation of lipolysis reducing large, intractable triglyceride and other fatty molecules to more readily metabolized, or mobilized free fatty acids and the like. Also, $\alpha_2$-receptor inhibition is believed to promote increases in fat lipogenesis, or fat production, in the adipocyte.

Proteins kinase C ("pkC") is believed to act independently to increase phosphodiesterase and reduce cyclic-AMP-levels, inhibiting lipolysis. Thus inhibition of the pkC receptor 14 is desirable, decreasing phosphodiesterase levels and permitting higher levels of cyclic-AMP to stimulate lipolysis.

Inventive topical application of Malvaceae extracts

Pursuant to this invention, it has been discovered that a combination of water-soluble and lipophilic extracts from a Malvaceae plant, when topically applied together or applied so as to act concurrently, are apparently effective at modifying the metabolism of adipocytes in a manner consistent with improving the cellulite condition. It may be postulated, without limiting the scope of the invention, that water-soluble phenolic and protein-rich Malvaceae extracts are apparently β-adrenergic simulators stimulating an increase the breakdown of fat. Malvaceae extracts rich in polar lipids appear to inhibit the production of fat in adipocytes, apparently through $\alpha_2$-inhibition, so that the combined extracts form a very effective cellulite treatment.

In an 8-week clinical study, reported in Table 3 below, a 44% reduction in the thickness of the fatty layer on subjects using a test product containing 1% Malvaceae lipids and 3% aqueous Malvaceae extracts was observed. Thigh girth was reduced 11% during the test period. These are very significant improvements that are difficult or impossible to obtain with known topically applied treatments in only eight weeks. The fact that such desirable results are obtainable with herbal, or plant origin active ingredients is a further significant advantage because many people prefer herbal materials and compositions that retain their natural complexity to isolated, chemically identified active substances.

Malvaceae Extracts: Preparation

Preferred for use as active ingredients in the practice of this invention are, in combination, an aqueous extract of a hibiscus plant and a lipophilic extract of the same plant source, preferably a Malvaceae plant, more preferably the species *Hibiscus Abelmoschus*. The desired fractions are prepared by careful selection of whole plants to avoid spoiled and diseased source material followed by pulverization, extraction with a suitable solvent system and filtration to provide a crude aqueous or lipophilic extract. The aqueous solvent system preferably includes, in addition to water, organic water-miscible solvents such as an alcohol or glycol or both. A preferred organic solvent system for extracting a lipophilic fraction can comprise one or more alcohols, acetone and at least one long-chain plant oil. The solvent extraction step should be carried out at elevated temperature and pressure, and in the case of the water-soluble extract, the pH should also be controlled.

Preferably, the crude extracts are purified and concentrated to yield consistent, well-characterized fractions. For example, the aqueous *Hibiscus Abelmoschus* extract can be purified and concentrated by differential extraction with the aqueous solvent system followed by dialysis and the lipophilic *Hibiscus Abelmoschus* extract can be purified, chromatographically using a sequential preparative column method. Preferred fractions of the aqueous *Hibiscus Abelmoschus* extracts are rich in proteins and polyphenols, while preferred lipophilic *Hibiscus Abelmoschus* extracts are rich in polar lipids, including cerebrosides and other sphingolipids.

Figure 2:
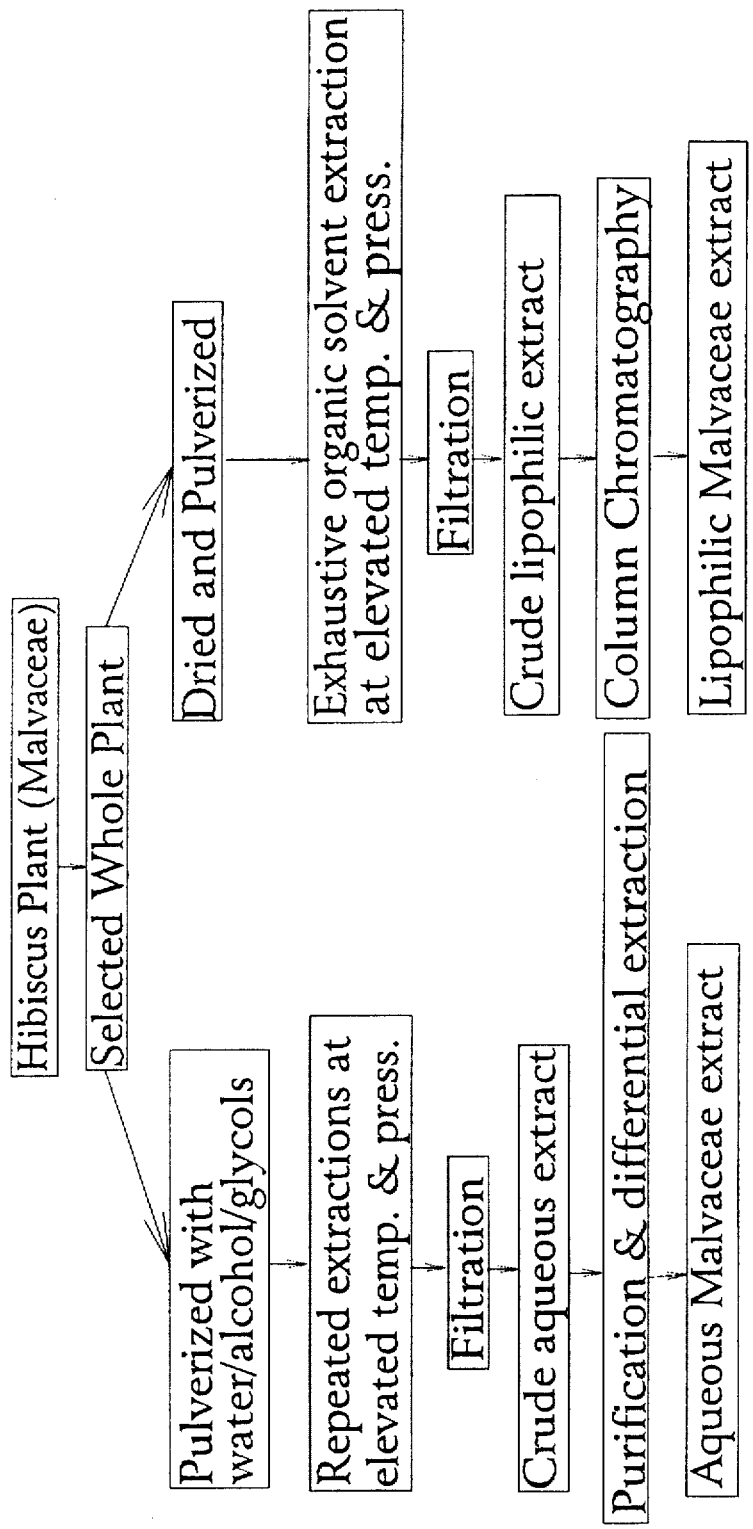
FIG. 2 is a schematic flow diagram illustrating a process of obtaining an aqueous and a lipophilic extract from hibiscus plants.

These extraction processes are illustrated schematically in FIG. 2. A refined hydrophilic Malvaceae extract produced by such a process and supplied by Plantech International Inc. is 100 percent aqueous in the sense that no organic solvents are employed in the extraction. The extract is standardized with polypeptides of molecular weight less than 5000 and is an odorless slightly yellowish liquid at room temperature with maximum solids contents of 1 percent by weight and a slightly acid to neutral pH in the range of from 5.8 to 6.8. The hydrophilic refined extract is described as being easily incorporated into the water phases of both skin and hair care formulations and is suggested for use in creams and lotions, cleansing gels, hydrophilic gels, bath products, shampoos and hair conditioners, liquid soap and body cosmetics. Such an aqueous *Hibiscus Abelmoschus* fraction is supplied by Plantech International Inc. under the name "hydroplasmatic extract".

A refined lipid extract of Malvaceae produced by such a process which is preferred for use in practicing the present invention is supplied by Plantech International Inc. and is a slightly milky/light amber oil with a slight characteristic odor that is compatible with oil and is soluble in water. The extract comprises at least 1% polar lipids, the lipid balance being non-polar, has an iodine value of from 35 to 45 and a specific gravity at 20 degrees C. in the range of from 0.80 to 0.90. Such a lipid *Hibiscus Abelmoschus* fraction is supplied by Plantech International Inc. under the name "Malvaceae Lipids PT2". Both extracts supplied by Plantech International Inc. are prepared from entire plants.

Chromatographic characterization of lipophilic extract

The refined lipophilic extract can be assayed by thin layer chromatography ("TLC") which separates the various lipid species present in a sample. Suitable TLC assay methods are known to those siallied in the art. In one method, by way of example, samples are prepared by dissolving aliquots of the lipophilic extract are thoroughly dissolved into a solvent system comprising a 2:1 mixture of chloroform and methanol, respectively, at a solids concentration of about 20–50 mg/ml.

For the TLC analysis, of 0.25 mm thick silica gel wafers, typically 10×20 cm. or 20×20 cm. are washed, activated and scored into 6 mm. lanes before use, in accordance with standard practice. Portions of lipid (50 ug) in solvent as above are applied 2 cm from the bottom of the TLC plates as small dots.

The chromatogram is first developed in a chloroform: methanol: water mixture (40:10:1) running 12 cm from the bottom of the plates and allowed to air dry. Next the plates are developed in a chloroform: methanol: acetic acid mixture (190:9:1) running to the top of the plates.

After air drying chromatograms are sprayed with a 50% sulfuric add and water mixture and heated to 220 C. (usually done by laying the TLC on a 1–2 inch thick aluminum block placed upon a hot plate). This visualizes the lipid species as they are charred and become brown.

Figure 4:
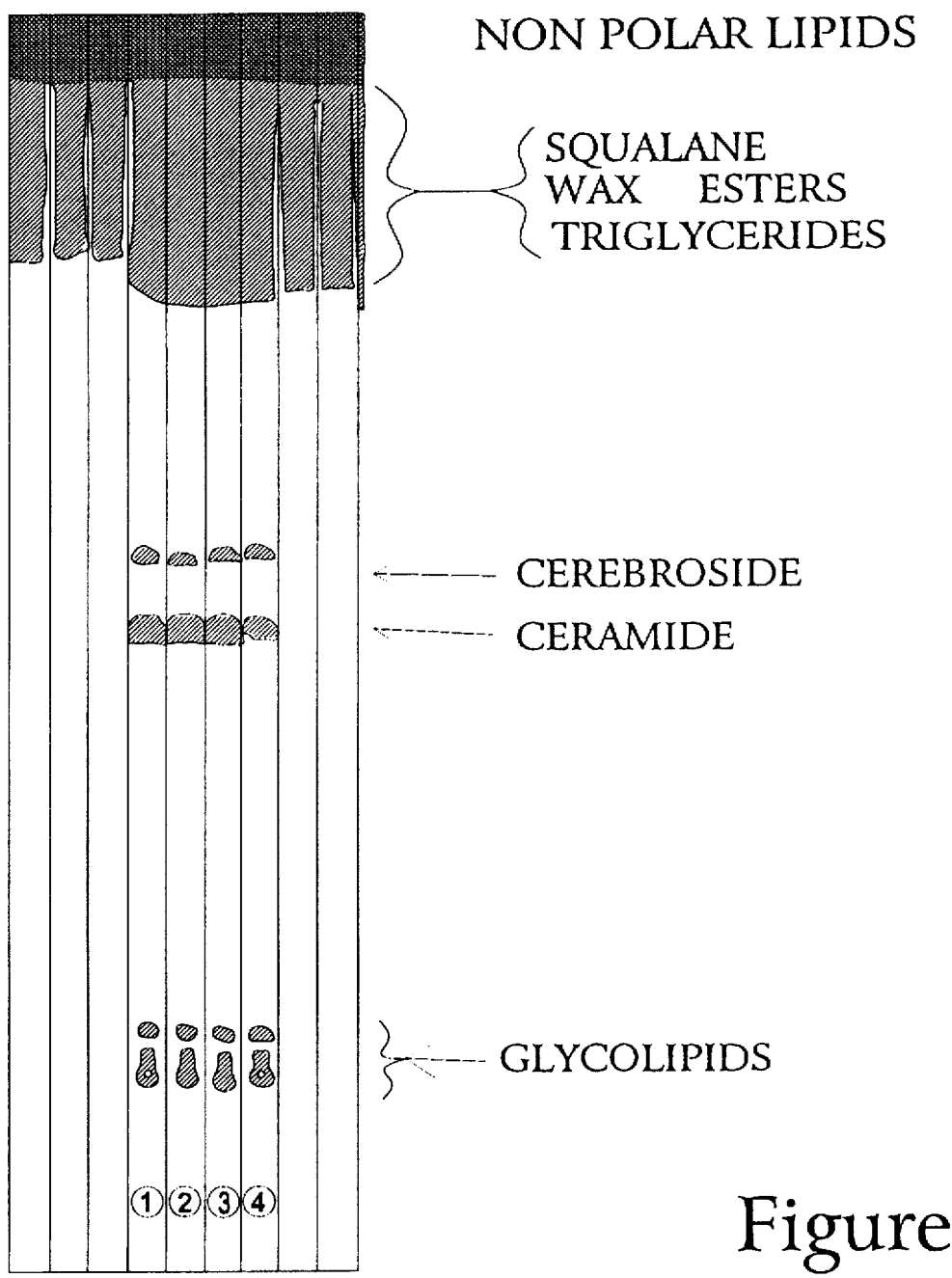
FIG. 4 is a schematic view of a chromatogram of a refined Hibiscus lipophilic extract.

Referring to the chromatogram of FIG. 4, a fast-moving group of lipids can be seen at the top of the plate. This is a complex, heterogeneous mixture of lipids including wax esters, hydrocarbons, triglycerides and squalane. In the middle of the plate, clearly defined bands can be seen which are identifiable as cerebrosides and ceramides, as labeled. An indeterminate group of very polar lipids which probably comprises mixed glycolipids, remains near the origin or the bottom of the plate.

Figure 5:
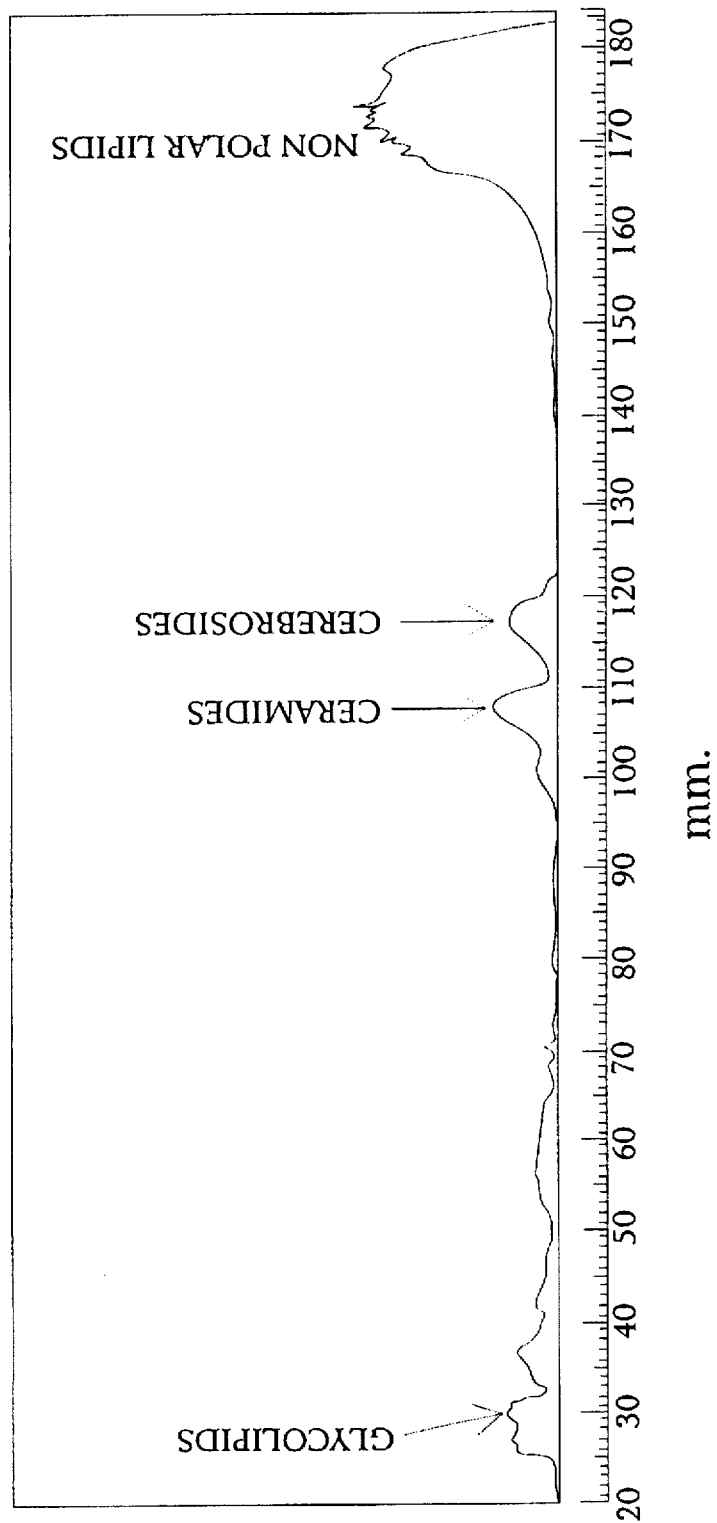
FIG. 5 is a graphic representation of the results of a densitometric scan of the chromatogram of FIG. 4.

The densitometric graph of FIG. 5 elucidates the chromatogram of FIG. 4 in more detail from which additional complexity of the lipophilic extract may be seen. For example to the right of the peaks characterized as glycolipids are several bumps of unidentified lipids. This complexity is characteristic of biological-sourced materials and demonstrates that the extract, though being a refined fraction is in no sense a specific fraction or purified isolate. The complexity is believed significant in the overall efficacy of the lipophilic extract in the practice of the invention, although it is possible that this efficacy lies principally with the presence of a few components, for example some glycolipids, the sphingolipids and at least a modest fraction of non-polar lipids, possibly in the approximate proportions suggested by chromatography.

Other Malvaceae plant sources

In the light of our discovery of the valuable in vivo fat-reducing and controlling properties of the described purified extracts of *Hisbiscus Abelmoschus*, it may be contemplated that other members of the large Malvaceae order, preferably, but not necessarily from the Hibiscus genus may have comparable useful properties, with more or less potency. Other Malvaceae genera include Malva, Althea, Hoheria, Sidalcea, Abutilon and Gossypium. Preferred aqueous extracts should be rich in proteins and polyphenols, and preferred lipophilic extracts should be rich in polar lipids including cerebrosides and other sphingolipids.

Useful refined extracts from such other plants must not have significant toxicity at effective concentrations. The extracts should also be cosmetically compatible in order to be formulated into suitable vehicles. So far as activity is concerned, the ultimate test is the ability to reduce or control fat deposits in vivo. From the data disclosed below, it may be concluded that an aqueous extract which provides an approximately 50% stimulation of lipolysis will be about as effective as known β-stimulants such as caffeine and the xanthines, and that higher simulations in excess of one hundred percent are obtainable with preferred extracts. Inhibition of lipid synthesis is more difficult and a relatively modest inhibition of about 25%, in the test described below, is valuable.

In evaluating lipophilic fractions from other Malvaceae species for use in the practice of this invention, fractions displaying comparable chromatograms to those of FIG. 4 or FIG. 5, may have good efficacy and be functional equivalents of the preferred extracts of the invention. Preferably, such equivalents contain both ceramide and cerebroside constituents. Preferably also, a comparable glycolipid constituent is present, optionally with at least some non-polar lipid fraction. Relative proportions as suggested by FIG. 5 are also preferable.

Malvaceae Extracts: Testing Determination of Adipocyte Metabolism

Glycerin release was used as a parameter to quantify lipolysis in actively metabolism adipocytes isolated from the thigh area of volunteers and evaluate various ingredients for their ability to stimulate adipocyte β receptors.

Refined, or purified Malvaceae extracts comprising preferred aqueous or lipophilic fractions as described above, and some known β-adrenergic stimulators used in anticellulite treatments, namely the xanthines aminophylline, caffeine and theophylline, were tested. Also tested, for comparative purposes, were a crude *Hibiscus Abelmoschus* extract and a herbal ingredient that has been used in anticellulite compositions, ivy extract. The results are reported in Table 1, below. Each agent was tested at several different concentrations, the results for the most effective concentration being reported.

TABLE 1

Effect of Test Materials on Lipolysis

| Test material | Maximum. stimulation % | Concentration at maximum stimulation mg/ml | Elevation of cAMP % |
|---|---|---|---|
| aminophylline | 54.0 | 1.00 | ns |
| theophylline | 45.0 | 1.00 | ns |
| caffeine | 51.0 | 2.00 | ns |
| purified aqueous Malvaceae extract | 111.0 | 1.00 | >50 |
| lipophilic Malvaceae extract | none | na | ns |
| crude Malvaceae extract | 14.0 | 0.75 | ns |
| ivy extract | none | na | ns |

Lipolysis stimulation

Referring to Table 1, the above data indicate that, at the most effective concentration, the purified Malvaceae aqueous extract ingredient of the invention was more than twice as effective in stimulating lipolysis as was aminophylline, the best of the tested control materials. Aminophylline is a well-known ingredient of many popular cellulite treatments known as thigh creams and its principle benefit is its ability to stimulate lipolysis. Xanthines do not stimulate improvements in skin growth nor do they stimulate the growth and repair of blood vessels.

Neither the lipophilic extract of *Hibiscus Abelmoschus*, nor the ivy extract tested, displayed any significant lipolytic activity, while the activity of the crude extract was very modest compared with the potent stimulation of lipolysis induced by the purified aqueous Malvaceae extract. Higher concentrations of the crude extract were no more effective. The poor performance of the other tested herbal ingredients emphasizes the surprising nature of the potent lipolytic activity exhibited by the refined aqueous *Hibiscus Abelmoschus* extract.

cAMP elevation

As shown in the last column of Table 1, cAMP levels were also monitored. "cAMP" is cyclic adenosine monophosphate, or cyclic adenylic acid, an important rate mediator of many cellular processes. These results indicated that the aqueous Malvaceae extract increased cAMP levels by more than 50% which is consistent with its role as a potent β-receptor agonist stimulating lipolysis. Elevated cAMP levels are induced by blocking phosphodiesterase, and are associated with fat metabolism, or lipolytic processes.

Toxicity

In vitro toxicity studies with cells grown in culture demonstrated the purified aqueous *Hibiscus Abelmoschus* extract to be non-toxic according to an industry standard which regards as non-lethal materials that do not cause more than 50% death of cells at a concentration of greater than 15 mg/ml. The refined aqueous *Hibiscus Abelmoschus* extract only began to kill some cells at a concentration of 15 mg/ml, not show 50% mortality: it is therefore well within the standard of non-toxicity.

Inhibition of adipocyte lipid synthesis

The ability of test materials to inhibit lipid synthesis was monitored as an increased retention of fat that globules of isolated adipocytes exhibited, in order to evaluate the properties of the test materials for their ability to inhibit adipocyte $\alpha_2$-receptors and retard production of fats. The results obtained are reported below in Table 2.

TABLE 2

Effect of Test Materials on Adipocyte Lipid Synthesis

| Test Material | Maximum inhibition of adipocyte fat | Concentration at maximum inhibition | Toxic effects (conc.) |
|---|---|---|---|
| Aminophylline | none | na | na |
| Theophylline | none | na | na |
| Aqueous Malvaceae extract | none | na | na |
| Lipophilic Malvaceae extract | 56% | 5 mg/ml | >40 mg/ml |
| Bovine sphingolipids | 11% | 10 mg/ml | 20 mg/ml |
| Crude Malvaceae extract | 6% | 10 mg/ml | 20 mg/ml |

Lipogenesis inhibition

The above data show that lipophilic *Hibiscus Abelmoschus* extracts exhibit a striking ability to inhibit adipocyte fat production, which ability is unique and is not remotely matched by other test materials. Thus the refined lipophilic *Hibiscus Abelmoschus* extract showed a 56 percent inhibition of adipocyte fat whereas the closest control, bovine sphingolipids was less than 20 percent as effective as the refined *Hibiscus Abelmoschus* extract at twice the concentration. The potency of the crude *Hibiscus Abelmoschus* extract was even lower. No lipogenesis inhibition activity was exhibited by the tested xanthines, aminophylline and theophylline or by the refined aqueous *Hibiscus Abelmoschus* extract.

Toxicity

In addition, the lipophilic *Hibiscus Abelmoschus* extract showed less far less toxicity than any other tested material.

Because they have a significant sphingolipid content and sphingolipids are known to inhibit protein kinase C activity, it might be speculated that the inhibition of adipocyte lipid production reported for Malvaceae extracts was due to the sphingosine content of those extracts. However, the data contradict such a hypothesis. If inhibition of protein kinase C activity were implicated, lipolytic activity should have been stimulated, whereas the Table 1 data show that lipolysis was not promoted by the lipophilic *Hibiscus Abelmoschus* extract.

Furthermore, bovine sphingolipids, whose sphingolipid content would also inhibit protein kinase C activity and should therefore strongly inhibit adipocyte fat production pursuant to such speculation, exhibit only very modest inhibition of adipocyte lipogenesis. Additionally, monitoring of cAMP levels found no increased level of cAMP induced by the lipophilic Malvaceae extract.

The pronounced inhibition of adipocyte lipid synthesis by the lipophilic Malvaceae extract is unexpected.

In summary, the data in Tables 1 and 2 show that both the aqueous *Hibiscus Abelmoschus* extract and the lipophilic *Hibiscus Abelmoschus* extract have excellent cellulite treatment properties and that they are respectively more effective than other test materials including aminophylline and known adipocyte $\alpha_2$- and β-receptor modulators. The data also show that the crude *Hibiscus Abelmoschus* extract is not effective.

Cellulite Treatments Employing *Hibiscus Abelmoschus* Extracts

To take advantage of these valuable cellulite treatment properties, the invention provides methods of treating cellulite-afflicted tissues which comprise the topical application to the overlying dermal areas of treatment compositions containing either the individual extracts or both extracts.

The invention also provides novel cellulite treatment compositions having excellent anticellulite activity which comprise a mixture of both extracts as will be described more fully hereinbelow. This novel cellulite treatment composition rapidly provides significant reductions in cellulite which, without limiting the invention, can be attributed to a twin-pronged mechanism wherein lipolysis is stimulated by the aqueous *Hibiscus Abelmoschus* extract and lipogenesis is inhibited by the lipophilic *Hibiscus Abelmoschus* extract.

The *Hibiscus Abelmoschus* extracts are cosmetically compatible and suitable for incorporation in known topical creams, lotions and tonics having good aesthetic characteristics. Both refined extracts are nearly odor-free, have little color are stable and readily miscible with a respective aqueous or oily cosmetic phase. The refined extracts are incorporated in known cosmetic bases in proportions such as to produce useful results in treating cellulite, especially significant reductions of the sub-dermal fatty layers associated with cellulite, while avoiding excessively strong concentrations that could with time produce toxic, or other undesirable side-effects.

Cellulite treatment compositions incorporating either or both *Hibiscus Abelmoschus* extracts are intended for application with light or moderate rubbing or massage to the skin overlying cellulite-afflicted fleshy regions of the body, notably the thighs, buttocks abdomen and upper arms. Such application, according to the methods of the invention, is made daily, preferably twice daily, and is continued for a sufficient period to produce the desired reductions in cellulite symptoms. Depending upon the concentrations and presence of active adjuvants, as described below, that period will usually be at least four weeks before positive results become apparent to the user and at least eight weeks before they become significant and substantial. Most people will wish to continue the treatments for at least four further weeks and for several months beyond that providing a total treatment period of six or more months during which the topical cosmetic containing the refined *Hibiscus Abelmoschus* extract, or extracts, is applied.

Concentrations of refined extracts

Suitable concentrations in topically applied cosmetic bases of the refined extracts comprise from about 0.1 to about 10.0 percent by weight for each extract, based upon the weight of the resultant cosmetic composition. A preferred range for the aqueous *Hibiscus Abelmoschus* extract is from about 1, more preferably 2, to about 5 percent by weight. For the lipophilic *Hibiscus Abelmoschus* extract a somewhat lower preferred range is from about 0.5 to about 3 percent with proportions close to one or two percent being preferred. Where mixed extracts are employed, the proportion may range up to about 15 percent by weight, subject to toxicity considerations.

Relative proportions of mixed extracts

Preferred cellulite treatment compositions according to the invention comprise a mixture of refined *Hibiscus Abelmoschus* extracts and, although an equal or lesser proportion of the lipophilic extract can be used, pursuant to the invention, it is also preferred that the to relative proportions of aqueous to lipophilic extract provide a substantial preponderance of aqueous extract. This is because the aqueous extract is substantially less expensive than the lipophilic extract and also appears to be somewhat less potent. The relative proportions may thus range from about 0.1 to 10 parts of aqueous extract per part of lipophilic extract, but a relative proportion in the range of 1 to about 7 parts of aqueous extract per part of lipophilic extract is preferred, with a range of from about two parts to about five parts aqueous extract per part of lipophilic extract being more preferred.

Rates of application

Suitable application rates of topically active agents can range from about 0.01 to 0.5 mg of active ingredients per square centimeter of skin, and such application rates are suitable for the active anticellulite refined *Hibiscus Abelmoschus* extracts employed in the present invention, with a range of from 0.05 to 0.2 mg/cm² being preferred. Liquid phase cosmetics are generally applied at rates of about 2–3 mg/cm², with thicker lotions and creams being spread at rates of up to about 5 or even 10 mg/cm². With a refined extract proportion in the applied cosmetic composition of from about 0.1 to no more than about 15 weight percent, this gives a possible rate of application of active ingredients of from about 0.002 mg/cm² to 0.45 mg/cm² in liquids, or to a maximum of about 1.5 mg/cm² in cream form, although rates at the limits of these ranges are not preferred. A preferred range is from about 0.01 to 0.5 mg/cm², with a range of from 0.05 to 0.2 mg/cm² active ingredient per unit skin area being more preferred.

Clinical Studies

A test cosmetic product according to the invention was formulated from a cosmetic base with about 1 percent refined lipophilic Malvaceae extract, rich in Malvaceae-derived sphingolipids, and with 3 percent refined aqueous Malvaceae extract, rich in proteins. The test product was evaluated over an eight week period on 10 subjects for its effect on cellulite and skin biophysical properties. Two control compositions employed an equivalent proportion of crude *Hisbiscus Abelmoschus* extract or 2 percent aminophylline, respectively, and an enhanced composition according to the invention incorporated a number of supplemental active ingredients including an alpha hydroxy acid to improve the skin.

For the clinical tests reported below, subjects were recruited examined and selected for those having cellulite afflictions in the thigh area. Subjects lacking bi-lateral symmetry were disqualified as the tests were left thigh versus right thigh comparatives.

A 5-point grading scale was used to rate the cellulite severity of each subject. The scale ranged from 0 to 4, as follows:

| | |
|---|---|
| 0 | No cellulite. |
| 1 | Small bumps or depressions. |
| 2 | Striations and bumps. |
| 3 | Pronounced lumpiness of the skin and striations. |
| 4 | All of the above plus hard sub-surface nodules. |

Subjects with grades 1 and 2 cellulite were chosen as this is the most responsive stage.

Subjects were restricted from using any product on the thigh area other than the test product, were instructed to use the test product twice per day at morning and at night, without undue massage. They were also weighed and instructed not to alter physical activity patterns. Any subject whose weight deviated over an eight week period by more than 5 percent was disqualified.

Thigh diameter was measured with a tape measure following a straightforward known procedure, substantially as set forth in Smith C & T. Fatty layer thickness, clinical grading and the other parameters listed in Table 3 were determined by known methods such as those reported in the Smith article. The data obtained from 10 subjects after 8 weeks of product use are reported in Table 3, below.

TABLE 3

Comparative Anticellulite Properties: changes in test parameters (except irritation)

| Parameters tested | Crude Malvaceae extract | 2% amino-phylline | Refined Malvaceae extracts (mixture) | Refined Malvaceae mixture + AHA |
|---|---|---|---|---|
| Thigh diameter | no change | −6% | −11% | −9% |
| Fatty layer thickness | −5% | −22% | −44% | −38% |
| Subjective improvement | +11% | +35% | +27% | +55% |
| Clinical grading | no change | +33% | +32% | +48% |
| Skin firmness: instrumental | −2% | +11% | +14% | +37% |
| Irritation reactions (grading) | 2 | 4 | 0 | 2 |
| Skin hydration | +25% | +22% | +19% | +84% |
| Surface smoothness | +15% | +14% | +11% | +69% |
| Skin firmness: subjective | +5% | +12% | +18% | +44% |

The refined *Hibiscus Abelmoschus* mix according to the invention, either with or without supplements, was very effective at improving the cellulite condition and was significantly more effective than the same base formula with 2% aminophylline. The crude *Hisbiscus Abelmoschus* extract produced little improvement in the fat-related cellulite characteristics of thigh diameter and fatty layer thickness. Both the supplemented and non-supplemented refined *Hibiscus Abelmoschus* extracts produced a much more dramatic reduction in these dimensions. The non-supplemented refined extract mixture was not perceived by the test subjects to be any better than aminophylline even although it caused much greater reductions in thigh diameter and fatty layer thickness.

However the refined *Hisbiscus Abelmoschus* extract mixture supplemented with AHAs to improve the skin condition by stimulating skin cell renewal, was perceived by the subjects to be dramatically better than any other test composition. The reason for this is apparent from the data in the lower half of the table which show that the supplemented extract mixture produced improvements in skin hydration, firmness and smoothness that were very significantly better than any other tested material.

It can be concluded from the Table 3 data that the combined *Hibiscus Abelmoschus* extracts are clinically shown to be effective cellulite treatments, to be substantially more effective than aminophylline and to be even better when supplemented with a skin renewal or improvement agent such as an AHA.

Supplemental active ingredients

As described, the invention provides a cellulite treatment composition and method which employ a combination of a particular completely aqueous extract of *Hibiscus Abelmoschus* or other equivalent hibiscus plant with a refined lipid extract of the same plant which after 4, or preferably 8, weeks of continuous daily topical application increase the ratio of lipolysis to lipogenesis and have a positive effect in reducing cellulite. The positive results are measurable as reductions in the thickness of the subcutaneous fatty layer determined, for example, by careful comparative measurements of thigh diameters.

The use of a combination of refined aqueous and lipid extracts or fractions of *Hibiscus Abelmoschus* has been found particularly effective in directly attacking the fatty deposits associated with cellulite, apparently by both increasing lipolysis and reducing lipogenesis.

This beneficial action can be enhanced by supplementation of the treatment with active agents that help improve microcirculation, improve skin condition or reduce fluid retention.

Skin cell renewal

Of particular value are ingredients that increase skin cell renewal and thus improve the condition of the skin, increasing its thickness and firmness, in quantities known to be effective. Some examples of such ingredients are 0.1–20 percent by weight of the composition of alpha hydroxy acid, for example lactic acid, preferably at a pH of the composition of from 3–6, pH-adjusting agents being included as necessary; a retinoid, for example from 0.1–3 percent vitamin A palmitate, which has good shelf life; or a biological cell renewal stimulant for example, 0.1–5 percent biopeptide (Sederma Laboratories).

Exfoliatives

Also of value are exfoliatives which improve the appearance of the skin and may help stimulate skin cell renewal. Mechanical exfoliatives such as nylon spheres or crushed abrasive organic matter, for example apricot pits, can be incorporated in effective proportions, as known to those skilled in the art, for example from about 1.0–20.0 percent by weight of the composition, preferably from about 5.0–10.0 percent.

Vasoactives

Vasoactive ingredients which stimulate an immediate increase in blood flow such as methyl nicotinate, butcher's broom, Peristan (Laboratory Serobiologic) or Mate extract are valuable in producing an immediate response and positive psychological perception. Such vasoactives may also assist in delivering the active ingredients to the vicinity of the fatty deposits.

Antioxidants

Antioxidants are also valuable to help reduce oxidative or free-radical damage, reduce irritation and moderate the ill effects of subcutaneous toxins. Examples of suitable antioxidants are vitamins C and E, BHT and propyl gallate in proportions known to be effective, for example from 1–5 percent by weight of the composition.

Moisturizers

Moisturizers such as emollient oils and hyaluronic acid or sodium hyaluronate are valuable to enhance the feel of a topical application and to improve the skin surface as well as to counter possible drying effects of other ingredients, for example, AHAs. Conventional proportions of from about 2 to about 12 percent by weight of the composition can be used.

Multi-functional Herbal Anticellulite Composition

The above-described and tested supplemented *Hibiscus Abelmoschus* extract composition demonstrated excellent objectively measured and subjectively perceived cellulite treatment properties, but because of the presence of an alpha hydroxy acid as an active agent would not be regarded as a strictly herbal composition by herbalists and people preferring or requiring herbal or biological treatments. It would therefore be desirable to provide a composition of comparable efficacy to the supplemented refined *Hibiscus Abelmoschus* extract mixture which also provided substantial structural skin improvements but which obtained these improvements from herbal supplements.

It would also be desirable to provide a cellulite treatment composition which has a comprehensive multi-functional mechanism of action. Cellulite is a multi-faceted, complex phenomenon of which sub-dermal fatty deposits and poor skin condition are just two symptoms.

A "cellulite vicious circle"

Figure 3:
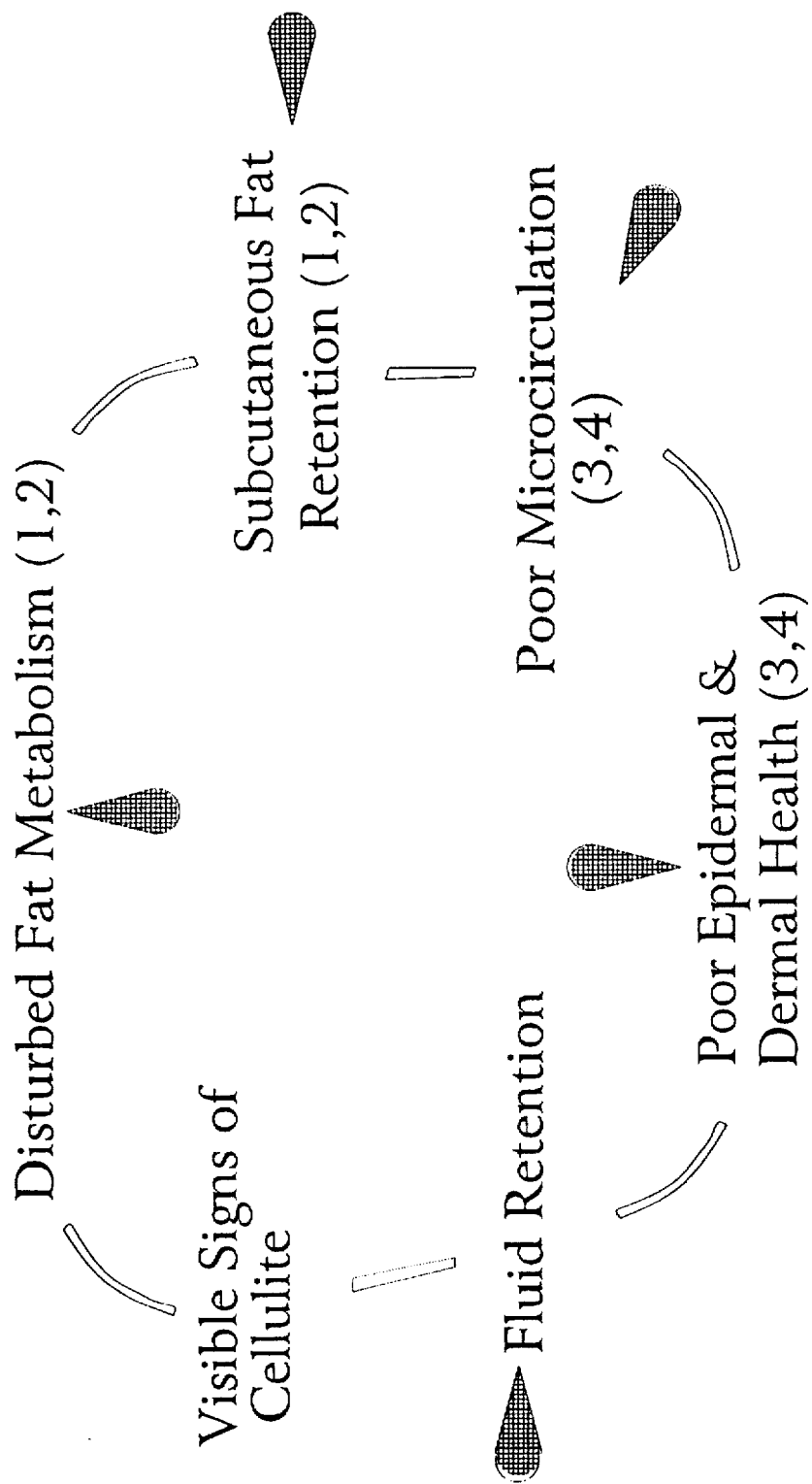
FIG. 3 is a diagrammatic model of a possible mechanism of action of a cellulite treatment composition according to the invention.

FIG. 3 indicates schematically a "cellulite vicious circle" of cause and effect. Thus, disturbed fat metabolism leads to subcutaneous fat retention which encroaches on the microvasculature, displacing and constricting it leading to poor microcirculation which in turn reduces the blood flow to the dermis and epidermis. The deteriorated skin caused by the poor blood flow leads to retention of fluid. Together these phenomena create the visible signs of cellulite. The blatant manifestation of unsightly symptoms frequently produces negative psychological effects upon the afflicted subject, leading to undesirable behavioral changes such as poor eating habits and lack of exercise which, in milder form, may have initiated the disturbances in fat metabolism in the first place. Thus the cellulite cycle feeds upon itself.

The numbers in parentheses in FIG. 3 refer to active ingredients in a further example of the compositions of the invention, described below, and serve to indicate upon what stage of the cellulite circle a particular anticellulite agent is active. The first two such active agents are the refined lipophilic *Hibiscus Abelmoschus* extract (1) and the refined aqueous *Hibiscus Abelmoschus* extract (2). As indicated in FIG. 3, these extracts are effective to modulate fat metabolism to correct disturbances and to reduce subcutaneous fat retention. However, they do not attack the accompanying symptoms of poor microcirculation, poor epidermal and dermal health, and fluid retention. Clearly, all ingredients that have significant anticellulite efficacy will improve the visible signs of cellulite, eventually.

The following Example of a cellulite treatment composition according to the invention is designed with herbal ingredients to provide an optimal cellulite therapy employing natural biological active ingredients, by mounting a balanced attack on the five main cellulite symptoms shown in FIG. 3: disturbed fat metabolism; fat retention; poor microcirculation; skin deterioration and fluid retention.

To supplement the primary *Hibiscus Abelmoschus* extract ingredients, the invention provides a cosmetic formulation which also includes biologicals that are effective, or believed effective, treatments for poor microcirculation, for epidermal and dermal health and for fluid retention. Biopeptides or honey extract are suitable biologicals that can be included to stimulate improvements in the microvasculature and to improve skin condition or structure. Fluid retention can be treated by biological or herbal ingredients such as Echinacea or coneflower extract and extracts of algae or Mate. These activities are summarized in Table 4 below in which the parenthetical numbers correspond with the reference numerals in FIG. 3, to show which stage of the cellulite cycle each ingredient is intended to counter.

TABLE 4

Supplemental Anticellulite Ingredients

| Ingredient | Reference in Figure 3 |
|---|---|
| Aqueous *Hibiscus abelmoschus* extract | (1) |
| Lipophilic *Hibiscus abelmoschus* extract | (2) |
| Biopeptide(palmitoyl tripeptide and polymethacrylate) | (3) |
| Honey extract | (4) |
| Echinacea extract (coneflower) | (5) |
| Algae-aloe mix + Mate extract | (6) |

The following Example incorporates the foregoing ingredients into a cosmetic gel composition suitable for daily topical application by ordinary consumers without professional supervision.

EXAMPLE:
Multi-functional Herbal Cellulite Treatment composition

| Ingredient (CTFA Name) | % | Phase |
|---|---|---|
| Phase A | | |
| water | 45.9 | A |
| disodium EDTA | 0.1 | A |
| (6) algae/aloe mixture | 2.0 | A |
| ethoxydiglycol | 8.0 | A |
| polymethylmethacrylate | 1.0 | A |
| methyl paraben | 0.2 | A |
| Phase B | | |
| cetyl alcohol | 1.5 | B |
| (polyoxyethylene)$_2$ stearyl ether | 0.75 | B |
| dimethicone | 4.0 | B |
| cyclomethicone | 2.0 | B |
| propylparaben | 0.1 | B |
| Phase C | | |
| (4) honey extract* | 7.0 | C |
| (2) aqueous Malvaceae extract* | 5.0 | C |
| (6) Mate | 2.0 | C |
| (5) coneflower or Echinacea extract | 2.0 | C |
| sodium hyaluronate | 1.0 | C |
| Phase D | | |
| water | 2.0 | D |
| triethanolamine | 1.25 | D |
| Phase E | | |
| polyacrylamide + C13-14 - | 3.5 | E |

-continued

EXAMPLE:
Multi-functional Herbal Cellulite Treatment composition

| Ingredient (CTFA Name) | % | Phase |
|---|---|---|
| isoparaffin + laureth 7 C12-15 alkyl benzoate | 4.0 | E |
| Phase F | | |
| C12-15 alkyl benzoate | 1.0 | F |
| (3) TBD biopeptide | 0.2 | F |
| tocopheryl acetate | 0.25 | F |
| (1) lipophilic Malvaceae extract | 1.0 | F |
| Phase G | | |
| imidazolidinyl urea | 0.4 | G |
| water | 2.0 | G |
| FD & C Blue #1 | 0.05 | G |

*Plantech Trading Inc.

To prepare the composition, the phase B ingredients are added to the phase A ingredients at about 80° C. with mixing, using a homogenizer. When thoroughly mixed to a homogeneous phase, phase °C. ingredients are slowly added to the mixture, with mixing. Phase D and phase E ingredients are successively added in a similar manner. Mixing, still at about 80 degrees °C. is continued until smooth. Using a propeller mixer the composition is cooled to 60° C. and phase F ingredients are added. It is then cooled to 50° C. and phase G and H ingredients are successively added and the complete composition is cooled to room temperature with propeller mixing.

The resultant product is an esthetic, white to off-white cosmetic cream composition and having a mild agreeable odor and good shelf life. The product is formulated entirely with herbal active ingredients to have multifunctional anticellulite properties.

A commercial herbal cellulite treatment product from Dior, sold under the trademark SVELTE, recites four herbal active ingredients, namely, (extracts from) terminalia sericia and yisnaga vera to slim the thigh area and kola nut, a caffeine-containing extract, plus plectranthus to maintain an ideal lipid or fat balance. Tests conducted on this Dior SVELTE product as described and reported in connection with Table 3, hereinabove, gave the following results in comparison with the preferred embodiment of the invention comprising both lipophilic and aqueous refined *Hibiscus Abelmoschus* extracts together with AHAs:

TABLE 5

Comparative Anticellulite Properties: changes in test parameters (except irritation)

| Parameters tested | Dior SVELTE | Refined Malvaceae mixture + AHA |
|---|---|---|
| Thigh diameter | -7% | -9 |
| Fatty layer thickness | -17% | -38 |
| Subjective improvement | +24% | +55% |
| Clinical grading | +37% | +48% |
| Skin firmness: instrumental | +7% | +37% |
| Irritation reactions (grading) | | 2 |
| Skin hydration | +37% | +84% |
| Surface smoothness | +21% | +69% |
| Skin firmness: subjective | | +44% |

It can be seen that the inventive embodiment provided better results in every test, in some instances, for example, all-important fatty layer thickness, dramatically better results.

INDUSTRIAL APPLICABILITY

The present invention is particularly suitable for application in the cosmetics, body shaping and health spa industries providing new and useful commercially marketable cellulite treatment compositions and methods of treating cellulite.

While an illustrative embodiment of the invention has been described above, it is, of come, understood that various modifications will be apparent to those of ordinary skill in the art. Such modifications are within the spirit and scope of the invention, which is limited and defined only by the appended claims.

We claim:

1. A cellulite treatment composition comprising:
   a) a cosmetic base;
   b) from about 0.1 to about 10.0 percent by weight of the treatment composition of a refined aqueous extract of *Hibiscus Abelmoschus* rich in proteins; and
   c) from about 0.01 to about 10.0 percent by weight of the treatment composition of a refined lipophilic extract of *Hibiscus Abelmoschus* rich in sphingolipids said refined extracts being present in a relative proportion of from about 1 to about 7 parts of aqueous extract per part of lipophilic extract;
   said composition being topically effective when applied to cellulite afflicted tissue to reduce fatty tissue deposits.

2. A cellulite treatment composition according to claim 1, being a cosmetic composition intended for daily topical application and providing a significant measurable improvement in cellulite after at least 8 weeks of such daily topical application, said composition comprising, in proportions by weight, from about 2 to about 5 percent of said refined aqueous *Hibiscus Abelmoschus* extract, from about 0.5 to about 3 percent of said lipophilic *Hibiscus Abelmoschus* extract, said composition being effective to stimulate adipocyte lipolysis and to inhibit adipocyte fat production.

3. A cellulite treatment composition comprising:
   a) a cosmetic base;
   b) a sufficient quantity of a refined aqueous extract of a plant species of the Malvaceae order to stimulate adipocyte lipolysis when said composition is applied topically to cellulite-afflicted tissue; and
   c) a sufficient quantity of a refined lipophilic extract of said plant species to inhibit adipocyte lipogenesis when said composition is applied topically to cellulite-afflicted tissue.

4. A cellulite treatment composition according to claim 3, being a cosmetic composition intended for daily topical application and providing a significant measurable improvement in cellulite after at least 8 weeks of such daily topical application, said composition comprising, in proportions by weight, from about 2 to about 5 percent of said refined aqueous *Hibiscus Abelmoschus* extract, from about 0.5 to about 3 percent of said lipophilic *Hibiscus Abelmoschus* extract, said composition being effective to stimulate adipocyte lipolysis and to inhibit adipocyte fat production.

5. A cellulite treatment composition according to claim 2, supplemented with an effective quantity of an active agent or agents to improve microcirculation, improve skin condition or reduce fluid retention.

6. A cellulite treatment composition according to claim 4 comprising one or more supplements selected from the group consisting of from about 0.1–20 percent by weight of the composition of an alpha hydroxy acid, the composition having a pH of from 3–6; a retinoid, in a proportion of from 0.1–3 percent vitamin a palmitate; from about 0.1–5 percent by weight biopeptide; from about 1.0–20.0 percent by weight of a mechanical exfoliatives; from about 1.0–5.0 percent by weight of a vasoactive ingredient; from about 1.0–5.0 of an antioxidant; and from about 2 to about 12 percent by weight of a moisturizer.

7. A method of treating cellulite-afflicted tissue comprising the topical application of a cosmetic composition containing a sufficient quantity of a refined aqueous extract of *Hibiscus Abelmoschus* to stimulate adipocyte lipolysis.

8. A method according to claim 7 wherein from about 0.1 to about 10.0 percent be weight of the aqueous extract of *Hibiscus Abelmoschus* is applied daily for at least four weeks.

9. A method according to claim 8 wherein the aqueous extract of *Hibiscus Abelmonschus* is applied daily for at least eight weeks.

10. A method according to claim 7 further comprising the topical application of a sufficient quantity of a refined lipophilic extract of *Hibiscus Abelmoschus* to inhibit adipocyte lipogenesis when said composition is applied topically to cellulite-afflicted tissue.

11. A method according to claim 10 wherein both the aqueous and lipophilic extracts of *Hibiscus Abelmoschus* are applied daily for at least eight weeks in a concentration of from about 0.1 to about 10.0 percent by weight of the applied composition.

12. A method of treating cellulite-afflicted tissue comprising the topical application of a cosmetic composition containing a sufficient quantity of a refined lipophilic extract, of *Hibiscus Abelmonschus* to inhibit adipocyte lipogenesis when said composition is applied topically to cellulite-afflicted tissue.

13. A method according to claim 12 wherein the lipophilic extract of *Hibiscus Abelmoschus* is applied daily for at least eight weeks in a proportion of from about 0.1 to about 10.0 by weight of the applied composition.

* * * * *